United States Patent
Mansouri et al.

(10) Patent No.: US 9,910,966 B2
(45) Date of Patent: Mar. 6, 2018

(54) SYSTEM AND METHOD OF INCREASING SAMPLE THROUGHPUT

(71) Applicant: Instrumentation Laboratory Company, Bedford, MA (US)

(72) Inventors: Sohrab Mansouri, Sudbury, MA (US); Jose Maria Cervera, Arlington, MA (US); Ashley Moraski, Hopkinton, MA (US)

(73) Assignee: Instruments Laboratory Company, Bedford, MA (US)

( * ) Notice: Subject to any disclaimer, the term of this patent is extended or adjusted under 35 U.S.C. 154(b) by 406 days.

(21) Appl. No.: 14/800,846

(22) Filed: Jul. 16, 2015

(65) Prior Publication Data

US 2015/0317457 A1    Nov. 5, 2015

Related U.S. Application Data

(63) Continuation of application No. 13/587,431, filed on Aug. 16, 2012, now Pat. No. 9,113,833, which is a continuation-in-part of application No. 13/210,810, filed on Aug. 16, 2011, now Pat. No. 8,560,251.

(51) Int. Cl.
*G06F 19/00* (2018.01)
*A61B 5/1495* (2006.01)
*A61B 5/145* (2006.01)
*G01N 33/50* (2006.01)
*G01N 33/487* (2006.01)
*G01N 35/00* (2006.01)
*G01N 27/327* (2006.01)
*C12Q 1/00* (2006.01)
*A61B 5/1486* (2006.01)

(52) U.S. Cl.
CPC .......... *G06F 19/366* (2013.01); *A61B 5/145* (2013.01); *A61B 5/1495* (2013.01); *G01N 33/48792* (2013.01); *G01N 33/50* (2013.01); *A61B 5/1486* (2013.01); *C12Q 1/002* (2013.01); *C12Q 1/006* (2013.01); *G01N 27/327* (2013.01); *G01N 2035/0097* (2013.01); *G01N 2035/00702* (2013.01)

(58) Field of Classification Search
None
See application file for complete search history.

(56) References Cited

U.S. PATENT DOCUMENTS

| | | |
|---|---|---|
| 5,112,455 A | 5/1992 | Cozzette et al. |
| 5,890,489 A | 4/1999 | Elden |
| 6,424,847 B1 | 7/2002 | Mastrototaro et al. |
| 6,615,064 B1 | 9/2003 | Aldrich |
| 6,652,720 B1 | 11/2003 | Mansouri et al. |
| 7,022,219 B2 | 4/2006 | Mansouri et al. |
| 7,087,149 B1 | 8/2006 | Muguruma et al. |
| 7,632,672 B2 | 12/2009 | Parnidi |
| 7,972,280 B2 | 7/2011 | Azer et al. |
| 8,042,073 B1 | 10/2011 | Nnaji |
| 8,112,375 B2 | 2/2012 | Pav |
| 8,226,555 B2 | 7/2012 | Say et al. |
| 8,231,532 B2 | 7/2012 | Say et al. |
| 8,231,534 B2 | 7/2012 | Habu et al. |
| 8,560,251 B2 | 10/2013 | Mansouri et al. |
| 9,113,833 B2 | 8/2015 | Mansouri |
| 9,113,834 B2 | 8/2015 | Mansouri |
| 2002/0053523 A1 | 5/2002 | Liamos et al. |
| 2005/0130249 A1 | 6/2005 | Parris et al. |
| 2005/0203360 A1 | 9/2005 | Brauker et al. |
| 2006/0167351 A1 | 7/2006 | Isaacson et al. |
| 2007/0136834 A1 | 6/2007 | Greenbaum et al. |
| 2008/0102441 A1 | 5/2008 | Chen |
| 2008/0114549 A1 | 5/2008 | Schafer et al. |
| 2008/0215254 A1 | 9/2008 | Leiner et al. |
| 2009/0194432 A1 | 8/2009 | Deng |
| 2010/0049022 A1 | 2/2010 | Parris et al. |
| 2010/0168535 A1 | 7/2010 | Robinson et al. |
| 2012/0209566 A1 | 8/2012 | Idiart |
| 2012/0262298 A1 | 10/2012 | Bohm et al. |
| 2013/0046478 A1 | 2/2013 | Mansouri et al. |

(Continued)

FOREIGN PATENT DOCUMENTS

| | | |
|---|---|---|
| JP | 2005-520662 | 7/2005 |
| JP | 2008-82876 | 4/2008 |

(Continued)

OTHER PUBLICATIONS

Patent Cooperation Treaty, International Search Report (ISR) & Written Opinion of the ISR, International Application No. PCT/US2016/020185, dated Jun. 13, 2016; 15 pages.

(Continued)

*Primary Examiner* — Soren Harward
(74) *Attorney, Agent, or Firm* — Burns & Levinson, LLP

(57) ABSTRACT

Technologies for increasing sample throughput by predicting the end point response time of a sensor for the analysis of an analyte in a sample are disclosed. In one aspect, a system includes a sensor that generates data signals associated with the measurement of an analyte within the sample. A processor records appropriate data points corresponding to the signals, converts them to a logarithmic function of time scale, and plots the converted data points. The processor then determines a curve that fits the plotted data points and determines a curve fitting equation for the curve. Once the equation is determined, the processor extrapolates an end point response of the sensor using the equation. A value, such as analyte concentration, is then calculated using the extrapolated end point response.

10 Claims, 13 Drawing Sheets

(56) References Cited

U.S. PATENT DOCUMENTS

2013/0245401 A1 9/2013 Estes et al.
2016/0033340 A1 2/2016 Todd et al.

FOREIGN PATENT DOCUMENTS

JP 2010-530531 9/2010
WO 2001033195 5/2001

OTHER PUBLICATIONS

Looking at Data—Relationships cautions about correlation and regression Available online: https://www.stt.msu.edu/Academics/ClassPages/uploads/FS12/421-1/Lecture_ch2_part4.pdf.
McDonald, J.H. Handbook of 'Biological Statistics. (2008), Excerpt of pp. 205-210.
Motulsky, H.J. Prism 4 Statistics Guide. (GraphPad Software Inc., 2005). Excerpt of pp. 25-28.
Motulsky, H.J. Prism 4 Statistics Guide. (GraphPad Software, Inc., San Diego CA, 2005), 3 excerpted pages, with 2 pages of front matter.
Patent Cooperation Treaty, International Preliminary Report on Patentability, International Application No. PCT/US2012/051140, dated Feb. 18, 2014; 7 pages.
Patent Cooperation Treaty, International Preliminary Report on Patentability, International Application No. PCT/US2012/051049, dated Feb. 18, 2014; 5 pages.
Patent Cooperation Treaty, International Search Report (ISR) & Written Opinion of the ISR, International Application No. PCT/US2012/051049, dated Nov. 2, 2012; 9 pages.
Patent Cooperation Treaty, International Search Report (ISR) & Written Opinion of the ISR, International Application No. PCT/US2012/051140, dated Nov. 2, 2012; 13 pages.
Teaching Leverage, Outliers, and Influential Observations in Introductory Statistics Courses; David W. Martin; submitted to JSE 2012. pp. 1-19, Also available online at www3.davidson.edu/cms/Documents/.../ACAD_ECO_jse.pdf.
Wang, J. Glucose Biosensors: 40 Years of Advances and Challenges. Electroanalysis 13, 983-988 (2001).
Patent Examination Report No. 1 issued in counterpart Australian patent application No. 2012296458 dated May 27, 2016, 4 pages.
Patent Examination Report No. 1 issued in a related Australian patent application No. 2012296505 dated May 27, 2016, 3 pages.
Office action issued in counterpart Japanese patent application No. 2014-526209 dated Jun. 21, 2016, 7 pages (including English translation).
Examination Report issued in co-pending Australian Patent Application No. 2012296458, dated Feb. 22, 2017. 7 pages.
Examination Report issued in related Australian Patent Application No. 2012296505 dated Feb. 22, 2017. 6 pages.
D'Errico "Need help curve fitting logarithmic data" message 6 of 9 (2008) retrieved from the internet <URL: https://au.mathworks.com/matlabcentral/newsreader/view_thread/173449>, 2 pages.
Frost "Curve Fitting with Linear and Nonlinear Regression" (2013) retrieved from the internet <URL: http://blog.minitab.com/blog/adventures-in-statistics-2/curve-fitting-with-linear-and-nonlinear-regression>, 11 pages.
Extended Search Report for European Patent Application No. 15 194 985.6, dated Dec. 8, 2015, 5 pages.
A Review of Statistical Outlier Methods; Nov. 2, 2006; By; Steven Walfish; Pharmaceutical Technology. pp. 1-5. Also available online: http://www.pharmtech.com/pharmtech/content/printContentPopup.jsp?id=384716.
Bronshtein, et al. Handbook of Mathematics. Fifth edition. (Springer-Veriag, 2007). pp. 379-392.
Ch. 6—Kaohsiung University Prof. Ray-Bing Chen, Regression Analysis: Fall 2008 (Power-point files) pp. 1-33.

SYSTEM AND METHOD OF INCREASING SAMPLE THROUGHPUT

CROSS REFERENCE TO RELATED APPLICATION

This application is a continuation application of a co-pending application Ser. No. 13/587,431, entitled SYSTEM AND METHOD OF INCREASING SAMPLE THROUGHPUT, filed on Aug. 16, 2012, which is a continuation-in-part application of U.S. patent application Ser. No. 13/210,810, entitled SYSTEM AND METHOD OF INCREASING SAMPLE THROUGHPUT, filed on Aug. 16, 2011, now granted U.S. Pat. No. 8,560,251, issued on Oct. 15, 2013, the contents of each of which are incorporated in their entirety by reference for all purposes.

FIELD OF THE INVENTION

The present invention relates to increasing sample throughput or measurement reliability. In one instance, the present invention is more specifically related to a device, such as, but not limited to, an automated clinical analyzer of body fluids, such as blood, and method for increasing sample throughput through the analyzer by predicting the end point response of an electrochemical sensor that responds to the presence of an analyte in a body fluid sample or increasing measurement reliability by improving a regression (also referred to as a curve fit) by removing outliers and determining whether the regression is within expectations.

BACKGROUND OF THE INVENTION

In a variety of clinical situations, it is important to measure certain chemical characteristics of a patient's blood, such as pH, hematocrit, the ion concentration of calcium, potassium, chloride, sodium, glucose, lactate, creatinine, creatine, urea, partial pressure of O2 and/or CO2, and the like. These situations may arise in a routine visit to the doctor's office, in the surgical suite, intensive care unit, or emergency room. The speed with which the analytical response is obtained is important for determining therapy and therapeutic outcome. A delay in the response time of a sensor slows diagnosis, and, with it, the application of appropriate therapy. Such delays may impact prognosis and clinical outcome.

Electrochemical sensors such as those described in U.S. Pat. Nos. 6,652,720; 7,632,672; 7,022,219; and 7,972,280, the entire disclosure of each of which is incorporated herein by reference in their entirety and for all purposes, are typically used to provide blood chemistry analysis of a patient's blood.

Conventional microelectrodes generate electrical signals proportional to chemical characteristics of the blood sample. To generate these electrical signals, the sensor systems may combine a chemical or biochemical recognition component, such as an enzyme, with a physical transducer such as a platinum electrode. Traditional chemical or biochemical recognition components selectively interact with an analyte of interest to generate, directly or indirectly, the needed electrical signal through the transducer.

The selectivity of certain biochemical recognition components makes it possible for electrochemical sensors to accurately detect certain biological analytes, even in a complex analyte mixture such as blood. The accuracy and the speed with which these sensors provide a response are important features of automated clinical analyzers.

One of the goals of clinical sample analysis system manufacturers is increasing sample throughput. Recent innovations have focused their attention on reducing the end point response time of a sensor, which is the time the sensor takes to provide an end point response. In conventional clinical analytical systems, once the sensor provides an end point response, the response is provided to a computer, which performs various mathematical operations to convert the end point response to a concentration of an analyte within the body fluid sample. The time taken for the sensor to provide an end point response dictates the time for a sample to be analyzed, which ultimately, determines the sample throughput. Accordingly, there is a need to reduce the time required to analyze a body fluid sample to expedite diagnosis and therapeutic intervention.

SUMMARY OF THE INVENTION

The present invention overcomes the drawbacks of prior art devices and methods and is directed towards technologies for increasing sample, such as body fluid sample, throughput by predicting the end point response time of a sensor for the analysis of an analyte in the sample. According to various embodiments described herein, the present invention describes techniques for extrapolating an end point response of a sensor by determining a curve fitting equation derived from data signals generated by the sensor in response to being exposed to analytes in a sample. In various embodiments, the curve fitting equation is a polynomial in a logarithm of time (log (t)) and a predetermined value of the logarithm of time at which a critical point occurs is provided, the predetermined value providing a relationship between polynomial coefficients. In order to obtain a reliable extrapolation, the reliability of the curve fit is determined and improved by removing outliers and determining whether the regression is within expectations.

In various embodiments, the curve fitting equation will be a second degree logarithmic polynomial having a general form of $s(t)=a(\log(t))^2+b(\log(t))+c$, where a, b, and c are the polynomial coefficients, the critical point is an extremum point, and the predetermined value (V) provides a relationship between the polynomial coefficients b and a of the form $b=-2 aV$; the polynomial coefficients a and c being determined based on the converted data points and s(t) is the calculated sensor output at a particular time t.

In one aspect, a system for increasing sample throughput includes a sensor configured to generate a plurality of data signals associated with the measurement of an analyte within the sample. The system further includes a processor that the records data points corresponding to a particular time range within the kinetic region, converts the recorded data points to a function of time scale, and plots the converted data points. The processor then determines a curve that fits the plotted data points and determines a curve fitting equation for the curve. Once the curve fitting equation is determined, the processor extrapolates an end point response of the sensor using the curve fitting equation. A value, such as analyte concentration, is then calculated using the extrapolated end point response.

In one or more instances, the processor in the system for increasing sample throughput is further configured to determine and improve usefulness of the curve fitting equation corresponding to the analyte, irk one or more embodiments, determining and improving usefulness of the curve fitting equation includes determining an outlier candidate with a largest residual, comparing a residual of the outlier candidate with the largest residual to a predetermined residual limit, classifying the outlier candidate with the largest residual as an outlier if the residual of the outlier candidate with the largest residual is greater than the predetermined residual limit, obtaining a measure of effect of the outlier on the parameters of the curve fitting equation, comparing the measure of the effect of the outlier to a predetermined measure limit, incrementing an outlier count, if the measure of the effect of the outlier is greater than the predetermined measure limit, comparing the outlier count to a predetermined outlier number limit, if the measure of the effect of the outlier is greater than the predetermined measure limit and removing the outlier from the data points, if the measure of the effect of the outlier is greater than the predetermined measure limit, resulting in an analyzed set of data points. In one embodiment of the determining and improving usefulness of the curve fitting equation, the processor is further configured to determine a curve fitting equation that fits a series of data from the analyzed set of data points as a function of time and repeat the determining and improving usefulness of the curve fitting equation for the analyzed set of data points.

In another aspect, a method for increasing sample throughput includes receiving data signals generated by a sensor in response to being exposed to an analyte within a sample. Once the data signals are received, data points associated with the data signals are recorded. A series of data points corresponding to a portion of a kinetic region time range from the recorded data points are selected and then converted to a logarithmic function of time scale and plotted. A curve that fits the data points is generated and a second degree logarithmic equation for the curve is determined. Once the curve fitting equation is determined, the processor extrapolates an end point response of the sensor using the curve fitting equation. A value, such as analyte concentration, is then calculated using the extrapolated end point response.

In yet another aspect, a computer readable storage medium includes computer executable instructions for receiving data signals generated by a sensor in response to being exposed to an analyte within a sample. Once the data signals are received, data points associated with the data signals are recorded. A series of data points corresponding to a portion of a kinetic region time range from the recorded data points are selected and then converted to a logarithmic function of time scale and plotted. A curve that fits the data points is generated and a second degree logarithmic equation for the curve is determined. Once the curve fitting equation is determined, the processor extrapolates an end point response of the sensor using the curve fitting equation. A value, such as analyte concentration, is then calculated using the extrapolated end point response.

In one or more embodiments, a system for analyzing samples includes a sensor configured to generate a plurality of data signals associated with the measurement of an analyte within the sample. The system further includes a processor that the records data points corresponding to at least a particular time range within a kinetic region and determines a curve fitting equation that fits the series of data as a function of time. The processor also determines and improves usefulness of the curve fitting equation corresponding to the analyte.

Methods for using the system for analyzing samples and computer readable storage media having computer executable instructions for receiving data signals generated by a sensor in response to being exposed to an analyte within a sample and for determining and improving usefulness of the curve fitting equation corresponding to the analyte are also disclosed.

BRIEF DESCRIPTION OF THE DRAWINGS

These embodiments and other aspects of this invention will be readily apparent from the detailed description below and the appended drawings, which are meant to illustrate and not to limit the invention, and in which.

DESCRIPTION

Figure 1:
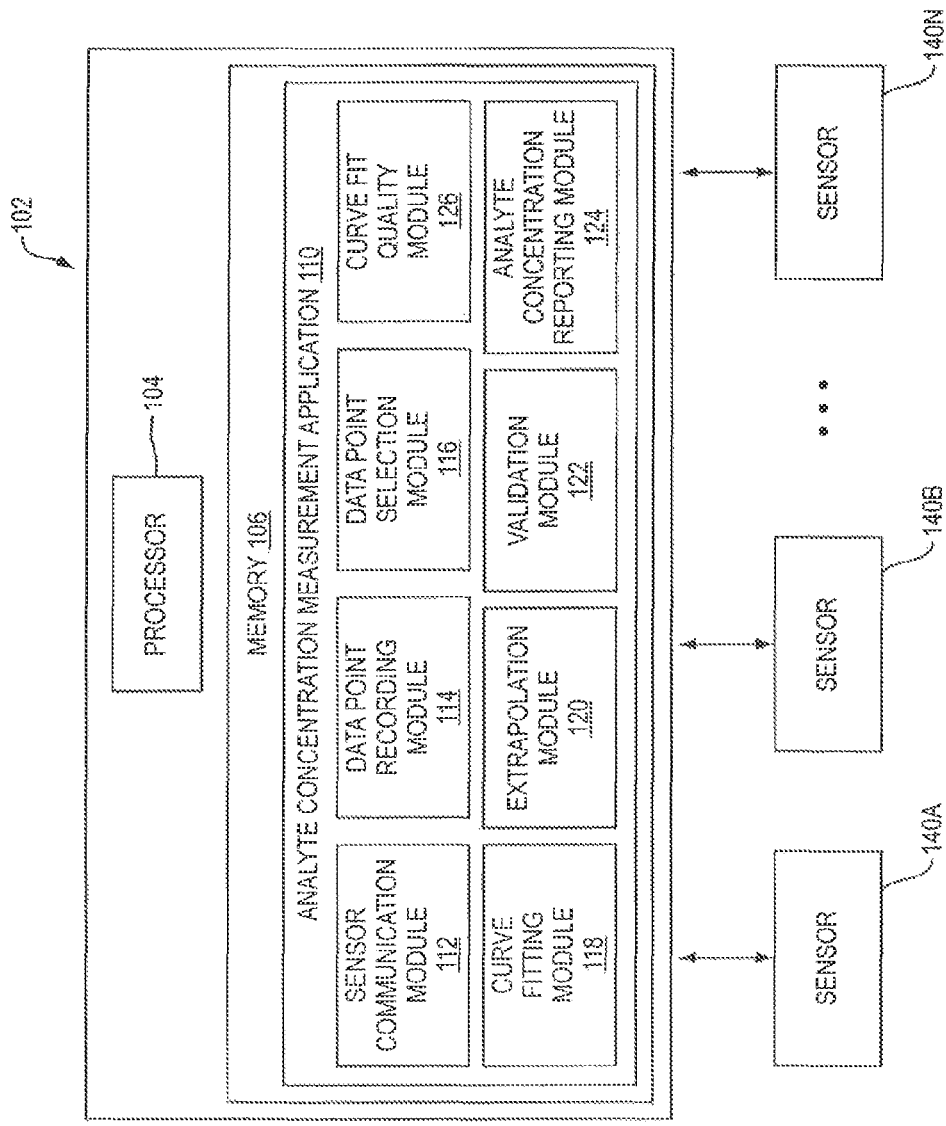
FIG. 1 illustrates an exemplary block diagram of an analyte concentration measurement system according to one embodiment of the invention.

The present invention is directed towards technologies for increasing sample, such as a body fluid sample, throughput in an automated clinical analyzer by predicting the end point response time of a sensor for the analysis of an analyte in the sample and for improving measurement reliability by detecting outliers and qualifying parameters in curve fitting equations. According to various embodiments described herein, the present invention describes techniques for extrapolating an end point response of a sensor by determining a curve fitting equation derived from data signals generated by the sensor in response to being exposed to a sample. In various embodiments, the curve fitting equation will be a second degree logarithmic polynomial having a general form of $s(t)=a(\log(t))^2+b(\log(t)+c$, where a, b, and c are the polynomial coefficients that are determined based on the converted data points, and s(t) is the calculated sensor output at a particular time t. In this way, a sample analysis system may no longer need to wait the entire duration of the sensor end point response time to analyze a sample and provide a determination of the concentration of the analyte measured by the sensor in the sample. Moreover, by reducing the sensor response time, and therefore, the sample exposure time, the sensor recovery time, which is the time the sensor takes to recover is also reduced, allowing for greater throughput.

The present invention will be more completely understood through the following description, which should be read in conjunction with the attached drawings. In this description, like numbers refer to similar elements within various embodiments of the present invention. Within this description, the claimed invention will be explained with respect to embodiments. The skilled artisan will readily appreciate that the methods and systems described herein are merely exemplary and that variations can be made without departing from the spirit and scope of the invention.

In order to further elucidate the present teachings, the following definitions are provided.

"Critical points," as used herein, refers to local extremum points and inflection points.

A "local extremum point," as used herein, refers to a point in a function at which the first derivative exists and is zero.

An "inflection point," as used herein, refers to a point in a function at which the second derivative changes sign.

An "outlier," as used herein, refers to a sample data point that is numerically distant from the rest of the data.

A "residual," as used herein, is the difference between a sample data point and the estimated function value as obtained by a curve fitting equation.

A "Studentized residual," as used herein, is the quantity resulting from the division of a residual by an estimate of its standard deviation.

"DFFITS," as used herein, is an expression that quantifies how influential a point is in a statistical regression. In its classical definition, DFFITS equals the Studentized residual times $\sqrt{h_{ii}/(1-h_{ii})}$, where $h_{ii}$ is the leverage for the point; leverage, $h_{ii}$, is defined as elements $h_{ii}$ of the Hat Matrix, H, which identifies the amount of leverage exerted by the ith observation $y_i$ on the ith fitted value. Another version of an expression that quantifies how influential a point is in a statistical regression is a measure that indicates the change at an extrapolated point caused by removing an individual point from the regression fit; examples of such measure, where 55 is the time corresponding to the extrapolated point are $$\text{Delta55}_i = \frac{[1 \quad \log_{10}55] * A * \begin{bmatrix} 1 \\ \log_{10}t \end{bmatrix} * R_i}{1 - H_{ii}}$$

For a linear fit in log(t) (where A is a matrix related to the Hat Matrix and defined as $$A = (X^T * X)^{-1})$$

and $$\text{Delta55}_i = \frac{[1 \quad \log_{10}55(\log_{10}55)^2] * A * \begin{bmatrix} 1 \\ \log_{10}t \\ (\log_{10}t)^2 \end{bmatrix} * R_i}{1 - H_{ii}}$$

For a quadratic fit in log(t). The above expressions are variations of the classical DFITTS or DFFITS$^2$.

"DFFITS," as used herein, refers to the classical definition or the measure that indicates the change at an extrapolated point caused by removing an individual point from the regression fit.

The "hat matrix, H," as used herein, sometimes also called projection matrix, is a matrix that maps the vector of observed values to the vector of fitted values.

Referring now to the figures, FIG. 1 illustrates a block diagram of an analyte concentration measurement system 102 according to one embodiment of the invention. In particular, an analyte concentration measurement system 102 may include a processor 104, a memory 106, and an analyte concentration measurement application 110 stored in the memory 106. The analyte concentration measurement application 110 may generally be configured to communicate with one or more sensors 140A-N, generally referred to hereinafter as sensors 140. In various embodiments, the sensors 140 may be electrochemical sensors that may generate voltmetric or amperometric signals in response to being exposed to analytes. In various embodiments, a first sensor 140A may be responsive to a first analyte within a sample, a second sensor 140B may be responsive to a second analyte within the sample, and an nth sensor 140N may be responsive to an nth analyte within the sample, and so forth. Further details regarding the sensors 140 are provided below.

The analyte concentration measurement application 110 may include one or more modules configured to perform specific functions or tasks in order to determine the concentration of an analyte within a sample. In various embodiments, the analyte concentration measurement application 110 may include a sensor communication module 112, a data point reporting module 114, a data point selection module 116, a curve fitting module 118, an extrapolation module 120, a validation module 122, an analyte concentration reporting module 124 and a curve fit quality module 126. It should be appreciated that in various embodiments, the analyte concentration measurement application 110 may include additional modules for performing additional tasks, or may include only some of the modules listed above.

The analyte concentration measurement application 110 may generally be configured to receive data signals generated by a sensor upon being exposed to an analyte within a sample, record data points extracted from the data signals, evaluate the data points on a function of time scale, a logarithmic function of time scale in one embodiment, determine a curve that matches the evaluated data points, determine a curve fitting equation that can be utilized to extrapolate an end point response of the sensor, and accurately estimate the concentration of the analyte based on the extrapolated end point response of the sensor.

In various embodiments, the sensor communication module 112 may be configured to receive data signals from the sensors 140. In some embodiments where the sensors may be electrochemical sensors, the data signals may represent an amperometric output that may be measured in Amperes, or a voltmetric output that may be measured in Volts. In various embodiments, these data signals may vary over time, and typically may generate an output value that eventually stabilizes over time. The stabilized output value may typically be the end point response of the sensor. It should be appreciated that any type of sensor that can generate a data output signal in response to being exposed to an analyte may be utilized as a sensor 140.

The data point recording module 114 may be configured to capture and record data points from the generated data signals. The data points may be stored in the memory of the analyte concentration measurement system 102, or at any other storage medium accessible by the analyte concentration measurement application 110. In various embodiments, the data point recording module 114 may record a measurement of the data signal after every nth fixed period of time. The fixed period of time may be predefined by the analyte concentration measurement application 110. It should be appreciated that the fixed period of time may be defined by the technological limitations of existing systems and is not intended to be limited to any particular range. However, in some embodiments, the fixed period of time may range from a millisecond to a few seconds. In alternate embodiments, the data point recording module 114 may record a measurement of the data signal after random or variable periods of time.

The data point selection module 116 may be configured to select pertinent data points from the recorded data points. In various embodiments, the data point selection module 116 may select data points that when plotted on a function of time scale, a logarithmic function of time scale in one embodiment, may allow the analyte concentration measurement application to determine a curve that closely fits the selected data points and also results in predicting an end point response of the sensor that is within acceptable limits. In various embodiments, data points that may provide the most accurate results may be selected from a time range that is empirically determined, and may vary depending on characteristics of the sensor and the analyte.

In various embodiments, the data point selection module 116 may select a series of data points corresponding to a kinetic region time range from the recorded data points. The kinetic region time range refers to any time range in which the data points are within the kinetic region of a sensor response. Typically, the kinetic region occurs from a first time when the sensor is exposed to the analyte, to a second time when the data signals generated by the sensor are not substantially similar to the end point response of the sensor i.e. before the sensor response reaches equilibrium. In other words, once the data signals generated by the sensor become substantially similar to the end point response of the sensor, the data signals are being generated in an equilibrium region. In various embodiments, the data point selection module 116 may select a series of data points corresponding to a portion of a kinetic region time range. In one embodiment, the time range may begin at about fifteen seconds after the sensor is exposed to the analyte. Moreover, the time range may end at about thirty seconds after the sensor is exposed to the analyte. Additional details regarding which data points to select are provided below with respect to FIG. 4.

The curve fitting module 118 may be configured, in one embodiment, to convert the selected data points to a function of time scale, a logarithmic function of time scale in one embodiment, such that the converted data points can be evaluated on a function of time scale. The curve fitting module may then determine a curve that closely matches the evaluated data points. The curve fitting module may use conventional curve fitting methods such as regression analysis or least square methods.

In various embodiments, the equation describing the curve (also referred to as the curve fitting equation) is a polynomial in a function of time, in one embodiment, a logarithm of time (log (t)), and a predetermined value of the function of time (in one embodiment, a logarithm of time) at which a critical point occurs is provided, the predetermined value providing a relationship between polynomial coefficients.

In various embodiments, the curve fitting module 118 may plot the selected data points on a logarithmic function of time scale, and determine a curve that closely matches or fits the plotted data points.

Upon determining the curve, the curve fitting module may determine a curve fitting equation corresponding to the curve. In various embodiments, the curve fitting equation is of the form $s(t)=a*(\log(t))^2+b*\log(t)+c$, wherein t represents time and a, b and c are fit parameters for a second order polynomial, the critical point is an extremum point, and the predetermined value (V) provides a relationship between the fit parameters b and a of the form $b=2aV$; the fit parameters a and c being determined based on the initial sensor response. The precise values of a, b, and c, which are determined empirically for each sensor configuration used, depend in part upon the concentration of the analyte, the size of the sample, the temperature, the geometry of the sensor apparatus setup, and other parameters.

In one instance, the invention not been limited to that instance, the predetermined value of the time at which time at which a critical point occurs is selected to be the time at which the end point is desired. In other instances, not a limitation of the invention, times beyond the endpoint time can be selected as the predetermined time.

The extrapolation module 120 may be configured to extrapolate an end point response of the sensor by solving the curve fitting equation for a time within the equilibrium region of the curve. In various embodiments, the analyte concentration measurement application 102 may empirical methods to determine a time that is within the equilibrium region of the curve, and then store the determined equilibrium region time as a predefined time with which to solve the curve fitting equation.

The validation module 122 may be configured to validate the calculated end point response by determining the coefficient of variation (CV) and the coefficient of determination ($R^2$). The following formulas for determining the coefficient of variation (CV) and the coefficient of determination ($R^2$) are well known in the art and may be used by the validation module 122 to validate the calculated end point response.

$$CV=\text{standard deviation}(y_i)/\text{mean}(y_i); \text{ and}$$

$$R^2=1(\text{sum}((y_i-f_i)^2)/(\text{sum}((y_i-\text{mean}(y_i))^2);$$

where $y_i$ and $f_i$ are the observed and calculated values at a specified time, respectively.

The curve fit quality module 126 may be configured to determine and improve usefulness of the curve fitting equation corresponding to the analyte. In one or more embodiments, the curve fit quality module 126 may be configured to, after the curve fitting equation has been obtained, to perform the analysis described herein below. The curve fit quality module 126 may be configured to determine an outlier candidate with a largest residual. Conventional methods for determining an outlier candidate with a largest residual, such as the Studentized residual or Dixon methods, can be used. Once the outlier candidate with largest residual is selected, the residual of the outlier candidate is compared to a residual limit. The residual limit can be predetermined from past experience, analytical considerations or other approaches. If the residual of the outlier candidate exceeds the residual limit, the outlier candidate is classified as an outlier. If the residual of the outlier candidate, which had the largest residual, is less than or equal to the residual limit, the curve fit quality module 126 can pass operation to another module since other residual candidates with similar residuals will also be within the residual limit, if the outlier candidate has been classified as an outlier, the curve fit quality module 126 is configured to obtain a measure of the effect of the outlier on the parameters of the curve fitting equation. Conventional methods for obtaining a measure of the effect of the outlier such as, but not limited to, Cook distance, DFFITS and DFBETAS, may be used. The measure of the effect of the outlier is compared to a predetermined measure limit. The measure limit can be predetermined from past experience, analytical considerations or other approaches. If the measure of the effect of the outlier exceeds the predetermined measurement limit, an outlier count, initially set to zero, is incremented, the outlier count is compared to a predetermined outlier limit, and the outlier is removed from the data points. A modified set of data points is obtained by removing the outlier or the outlier candidate from the data points and the above analysis is performed again.

It should be appreciated that by way of the present disclosure, the sample exposure time is reduced as the sensor response time is reduced. As a result of the reduced sample exposure time, the sensors, and in particular, enzymatic sensors, including but not limited to sensors for measuring glucose and lactate, may have shortened sensor recovery times. As the sensors can recover faster, a greater throughput can be achieved.

Exemplification

The following exemplary embodiments are presented to further elucidate the invention but it should be noted that the invention is not limited only to the exemplary embodiments.

The analyte concentration recording module 124 determines the concentration of the analyte within the sample using the calculated end point response and report the analyte concentration with a flag if the validation module 122 determines that the CV and $R^2$ are not within acceptable limits. Conversely, if the CV and $R^2$ are within acceptable limits, then the analyte concentration recording module 124 may report the concentration of the analyte without a flag. Analytes that may be measured according to the method of the invention include, but are not limited to for example, hematocrit, the ion concentration of calcium, potassium, chloride, sodium, glucose, lactate, creatinine, creatine, urea, partial pressure of O2 and/or CO2, or any other analyte for which a sensor exists. In various embodiments, the flag may be a data bit that may be represented visually as a flag, a symbol, or aurally, as a beep, a tone, or in any other manifestation that may indicate to a user that the either the CV or the $R^2$ is not within acceptable limits.

Figure 2:
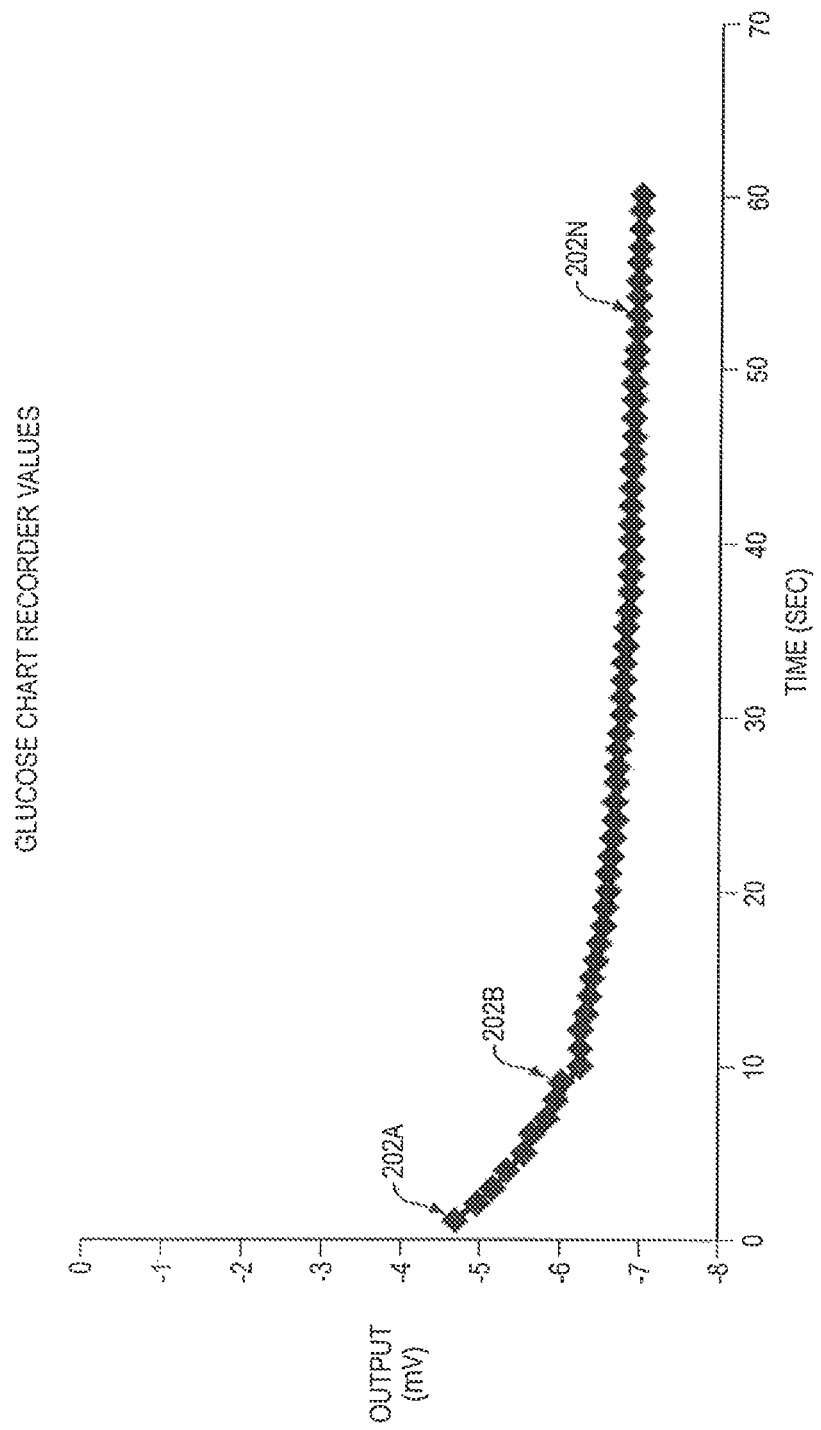
FIG. 2 shows an exemplary plot of voltage versus time for experimental data generated by a sensor for measuring the concentration of glucose according to one embodiment of the invention.

Referring now to FIG. 2, an exemplary plot of voltage versus time for experimental data generated by a sensor for measuring the concentration of glucose is shown. In particular, the plot shows a series of data points 202A-N that are captured from a data signal generated by the sensor 140. The data points indicate an output value, such as a voltage, current, or charge. In various embodiments, data points from the generated signal may be recorded over time and plotted against time. The plot shown in FIG. 2 is generated by plotting the recorded data points 202A-N against time. In the present embodiment, the data points are recorded every second. However, in various embodiments, data points may be recorded at time intervals that are less than or more than a second.

It should be appreciated that by recording data points at time intervals less than a second, more data is generated, which may allow for a more accurate plot, but may also utilize additional computing resources, which may be undesirable, depending on system resources. Alternatively, data points that are recorded at time intervals substantially exceeding a second may provide a less accurate plot. In any event, the length of the time intervals between data points is an implementation choice that may be determined based on various factors, such as the end point response time of the sensor, limitations with respect to computing resources, the nature of the sensor and analyte, and the like.

Figure 3:
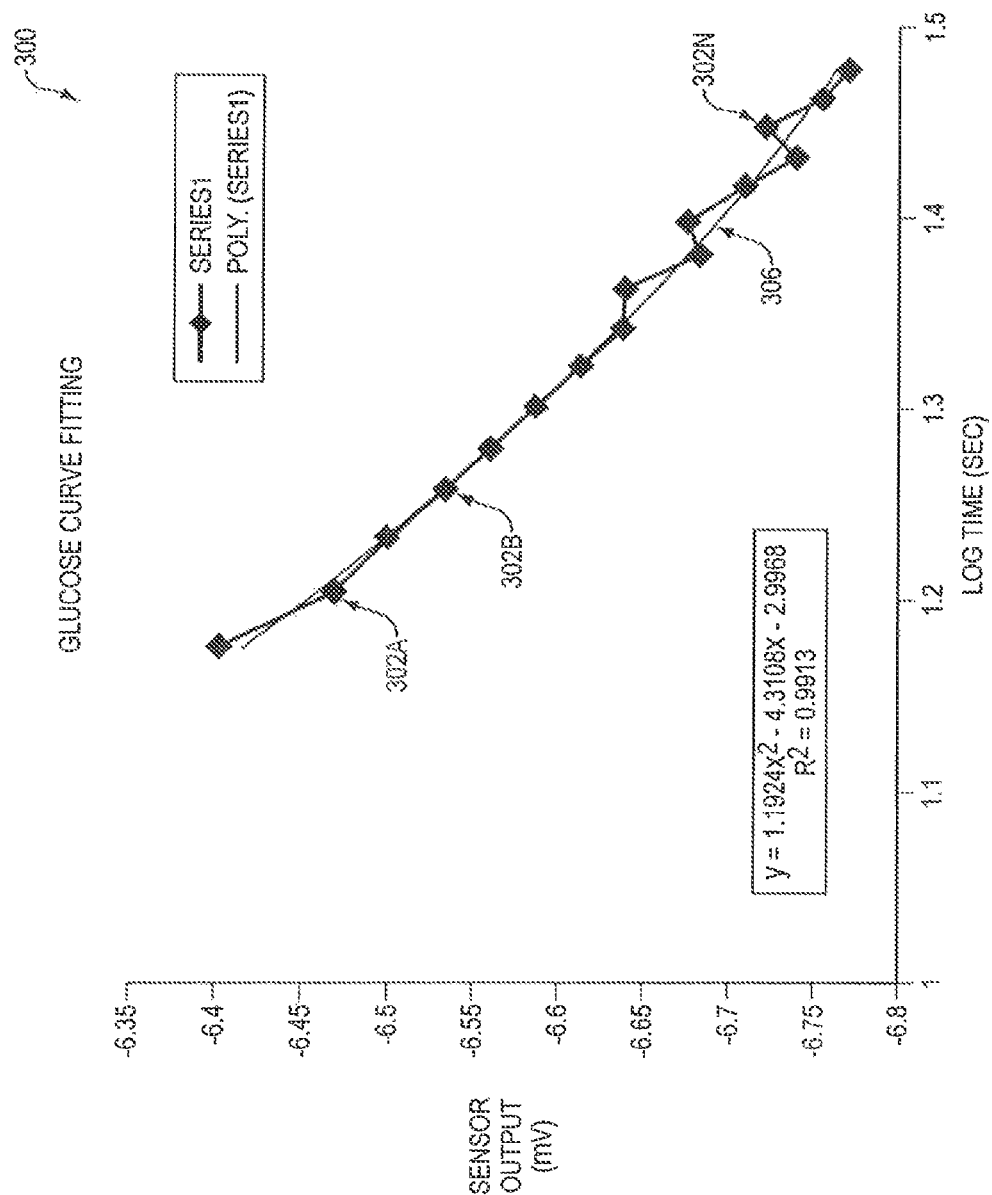
FIG. 3 shows an exemplary plot of voltage versus logarithmic function of time using a portion of the experimental data of FIG. 2 according to one embodiment of the invention.

Referring now to FIG. 3, an exemplary plot of voltage versus a logarithmic function of time using a portion of the experimental glucose data of FIG. 2 is shown. As described above, once the data points corresponding to the data signals received from the sensor are recorded, the data point selection module 114 may select pertinent data points from the recorded data points. The selected data points may then be converted to a logarithmic scale, such as base 10 or natural log. Upon converting the data points to the logarithmic scale, the converted data points 302A-N are plotted as voltage values versus logarithmic function of time.

As shown in FIG. 3, once the converted data points are plotted on the voltage versus logarithmic function of time scale, the plot 300 may be shown. This allows the curve fitting module 118 to determine a curve 306 that closely matches the converted data points 302A-N. Then, the curve fitting module 118 may determine a curve fitting equation based on the curve 306 that is simpler than existing curve fitting equations utilized in sensor technologies. Existing curve fitting equations require finding roots of non-linear equations, whereas the techniques disclosed herein do not require finding such roots. Finding roots of non-linear equations is computationally intensive, and when dealing with systems that have high throughputs, the severity of the problem becomes even more apparent. As a result, by utilizing curve fitting equations that do not require finding roots of non-linear equations, the analyte concentration measurement system 102 requires fewer computational resources than existing systems. This translates to various advantages over existing systems, including but not limited to increased throughputs, reduced costs of manufacture, and a smaller physical and energy footprint. Further, it should be appreciated that the display step may not be necessary as the curve fitting equation may be determined without having to plot data points or draw a curve that fits the data points.

According to various embodiments, the curve fitting equation may typically be a second degree logarithmic equation that has a general form of $$s(t)=a(\log(t))^2+b(\log(t))+c,$$

where a, b, and c are the polynomial coefficients that are determined based on the converted data points, and s(t) is the calculated sensor output at a particular time t. In one embodiment, a predetermined value of the logarithm of time at which a critical point occurs is provided, the predetermined value providing a relationship between polynomial coefficients. The precise values of a, b, and c, which are determined experimentally or analytically (for example, using regression analysis) for each sensor configuration used, depend in part upon the concentration of the analyte, the size of the sample, the temperature, the geometry of the sensor transducer setup, and other parameters, in one instance, the critical point is an extremum point, and the predetermined value (V) provides a relationship between the fit parameters b and a of the form b=−2 aV; the fit parameters a and c being determined based on the sensor response by curve fitting techniques (such as, but not limited to, regression analysis and least square methods). Once the values of a, b, and c have been determined for a sensor configuration, the curve fitting equation may be used to rapidly estimate the concentration of the analyte in the sample. According to the invention, there is no need to wait for the sensor to provide its final reading to determine the analyte concentration.

It should be appreciated that the selection of the data points to be converted plays an important role in determining the accuracy of the curve fitting equation. Although conventional wisdom would suggest that the greater the number of data points utilized for determining the curve fit, the better.

The present invention discloses that such wisdom is not necessarily true. Rather, the range from which the data points are selected may play an even more important role. In various embodiments, the data points selected to be converted to the logarithmic function of time scale were the data points generated from 15-30 seconds after the analyte was first exposed to the sensor. In other embodiments, data points from 15-35 seconds after the analyte was first exposed to the sensor were used without significant improvements in accuracy. Similarly, data points from 10-25 seconds after the analyte was first exposed to the sensor were used but produced some results that were not accurate enough. It should be appreciated that the data points selected may vary based on the type of sensor and analyte, end point response time, amongst other factors. In various embodiments, the time range for selecting the data points may be determined through empirical methods.

As described above, the end point response value of the sensor may be calculated by solving the equation for a time that is within the equilibrium region of the sensor response curve. Once the end point analyte related value is calculated using the curve fitting equation, the end point response value is converted to a value corresponding to the concentration of the analyte, using, for example, a method comprising a calibration value (e.g. a ration, a calibration point, a difference value, etc.).

Figure 4:
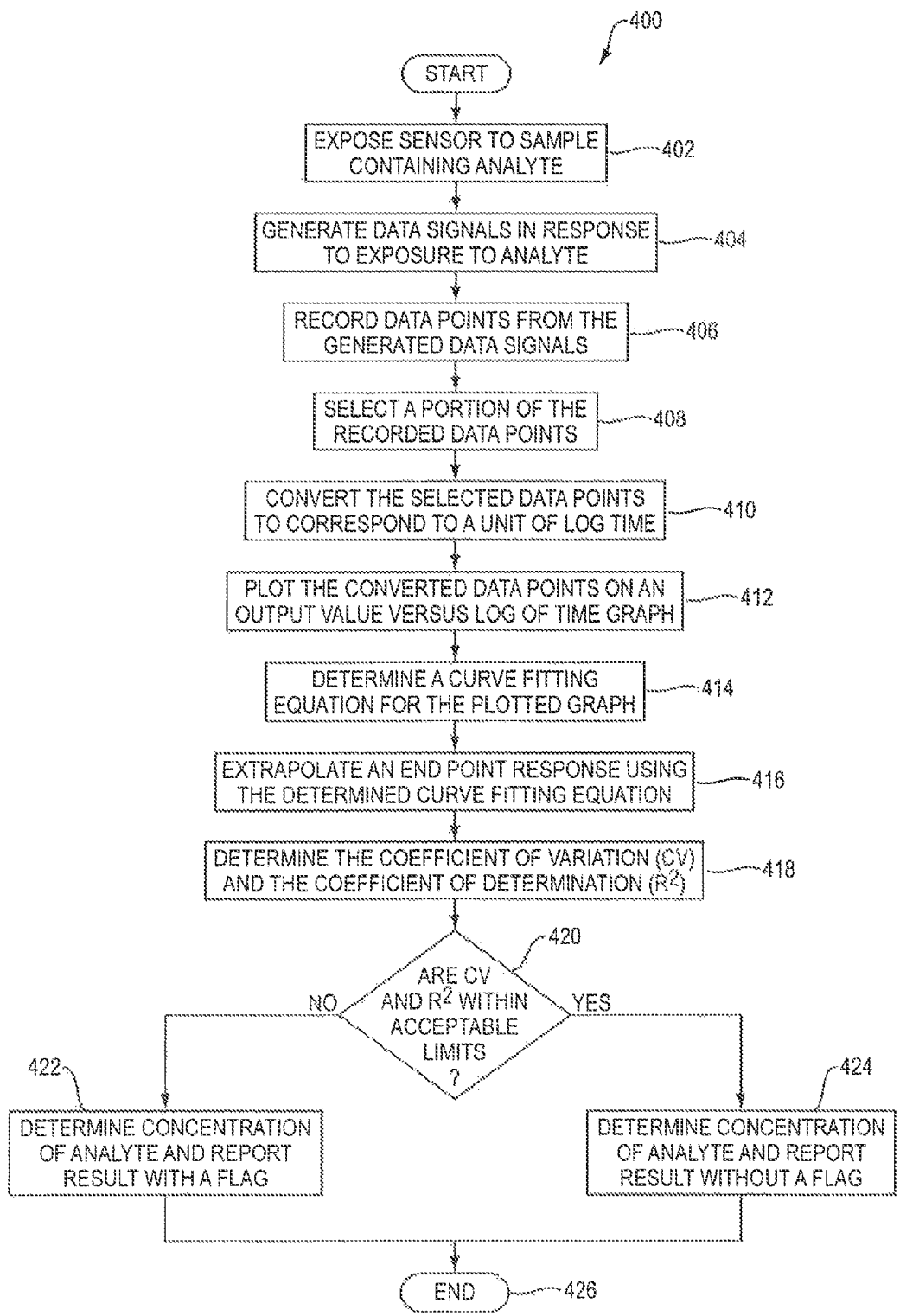
FIG. 4 is an exemplary logical flow diagram for predicting the end point response of the sensor according to one embodiment of the invention.

Referring now to FIG. 4, an exemplary logical flow diagram for estimating the concentration of an analyte within a sample is shown. A routine 400 begins at operation 402, where the sensor 140 is exposed to a sample containing the analyte. As described above, the electrochemical sensor 140 may be responsive to the levels of concentration of an analyte within the sample.

From operation 402, the routine 400 proceeds to operation 404, where the sensor 140 may generate one or more data signals in response to the exposure to the analyte, in various embodiments, the data signals may be in the form of a voltage, current, charge, or any other type of measurable output. These data signals are continuously being generated by the sensor 140 while being exposed to the analyte.

From operation 404, the routine 400 proceeds to operation 406, where the data point recording module 114 may record data points from the data signals. The granularity at which these data points are recorded may be determined by the type of sensor, the amount of analyte, the size of the sample, the temperature, amongst other factors. In one embodiment, the data signals are recorded every second. However, it should be appreciated that the frequency at which these data points are recorded may be greater than or less than one data point per second. The data points may be stored within the memory of the analyte concentration measurement system 102, or may be stored remotely at a location that is accessible by the analyte concentration measurement application 110.

From operation 406, the routine 400 proceeds to operation 408, where the data point selection module 116 may select a portion of the data points recorded by the data point recording module 114, in various embodiments, the data point selection module 116 may select data points that, when plotted, may help determine a curve that has an equation, which, when extrapolated to a time in the future, generates a result that is proximate to the actual result of the sensor 140. In various embodiments, the data point selection module 116 may select any number of data points. There is a countervailing balance that the data point selection module 116 has to consider when selecting data points. Selecting too many data points may also increase the number of outliers, which may adversely affect the accuracy of the curve being fitted, as well as selecting data points that are too far ahead in time may delay the time in which the analyte concentration measurement system 102 may determine the analyte concentration. In particular, selecting the first few data points that are recorded may cause the analyte concentration measurement system to produce inaccurate results. This is because the sensors 140, when initially exposed to the analyte, may generate noise signals, amongst other undesirable affects. Accordingly, based on empirical methods, data points selected from the kinetic region but after the initial response of the sensor 140 may generate the most accurate results, while balancing the need to determine the concentration of analyte in the shortest time, without significantly compromising on accuracy.

From operation 408, the routine 400 proceeds to operation 410, where the curve fitting module 118 converts the selected data points having an output value corresponding to a particular time to a unit of logarithmic function of time. In various embodiments, the base of the logarithmic scale may be base 10, or natural log (ln e). By doing so, a curve generated by the plotted converted data points may be more accurate and utilizes less data points than existing curve fitting equations.

From operation 410, the routine 400 proceeds to operation 412, where the curve fitting module 118 may plot the converted data points on a graph, in various embodiments, the Y-axis is an output value gathered from the data signal generated by the sensor 140, and the X-axis is a logarithmic function of time. From operation 412, the routine 400 proceeds to operation 414, where the curve fitting module 118 may determine a curve fitting equation for the plotted graph, in various embodiments, the curve fitting module 118 may determine a curve fitting equation that is a second degree logarithmic polynomial having the form $s(t)=a(\log(t))^2+b(\log(t))+c$, where a, b, and c are the polynomial coefficients that are determined based on the converted data points, and $s(t)$ is the calculated sensor output at a particular time t. The precise values of a, b, and c, which are determined experimentally or analytically for each sensor configuration used, depend in part upon the concentration of the analyte, the size of the sample, the temperature, the geometry of the setup, and other parameters. It should be appreciated that the curve fitting module may not necessarily plot the data points to determine a curve that fits the data points. In some embodiments, the curve fitting module 118 may be able to determine a curve that fits the data points without having to plot the data points. Commercially available curve fitting software may be utilized to determine a curve and a corresponding equation that fits the selected data points.

From operation 414, the routine 400 proceeds to operation 416, where the extrapolation module 120 extrapolates the calculated end point response of the sensor 140 by solving the curve fitting equation for a time that falls within the equilibrium region. From operation 416, the routine 400 proceeds to operation 418, where the validation module 122 validates the end point response for accuracy. According to some embodiments, the validation process includes determining the coefficient of variation (CV) and the coefficient of determination ($R^2$) using the formulas of CV and $R^2$ that are presented above.

From operation 418, the routine 400 proceeds to operation 420, where the validation module determines whether the CV and the $R^2$ are within acceptable limits predefined by the analyte concentration measurement system 102. In various embodiments, these limits may allow for the CV and $R^2$ to fall within an acceptable range, which may be known by those persons having ordinary skill in the art. In one embodiment, the limits may allow for the $R^2$ to fall between 0.98 and 1. The coefficient of determination ($R^2$) indicates how well the data and the curve fit function match. The closer the value of $R^2$, the better the match.

If, at operation 420, the validation module 122 determines that either the CV, $R^2$, or both the CV and $R^2$ not within the acceptable limit, the routine 400 proceeds to operation 422, where the analyte concentration reporting module 124 determines the concentration of the analyte using the extrapolated end point response, and reports the analyte concentration with a flag indicating that the result does not fall within the acceptable limits.

However, if at operation 420, the validation module 122 determines that both the CV and $R^2$ are within the acceptable limit, the routine 400 proceeds to operation 424, where the analyte concentration reporting module 124 determines the concentration of the analyte using the extrapolated end point response, and reports the analyte concentration without a flag. From operation 422 and 424, the routine 400 ends at operation 426.

According to various embodiments, it may be desirable to provide a system for calibration of the sensors 140. A self-calibration system for measuring the analyte concentration may be used to correct for imprecision in the manufacturing of the sensor, thus reducing the time and cost of manufacture. In addition, the self-calibration system may be used to compensate for small magnitudes of noise generated by the sensor or other components of the analyte concentration measurement system 102.

Figure 5A:
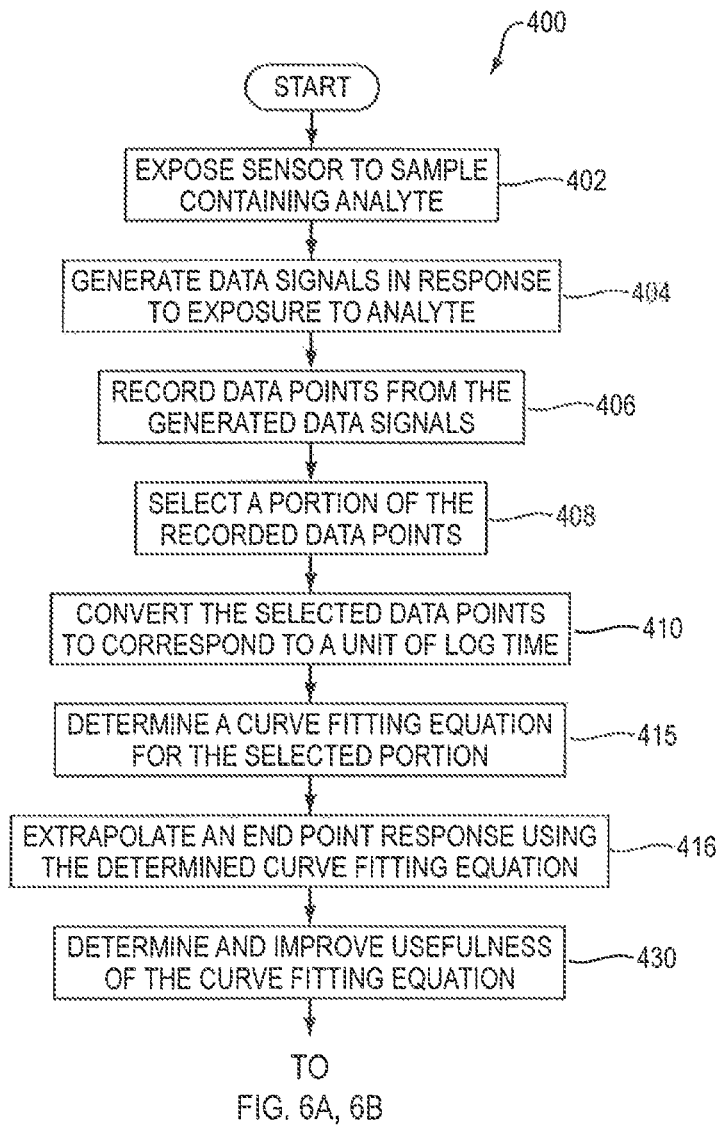
FIGS. 5a and 5b are exemplary logical flow diagram for analysis of samples according to embodiments of the invention.

Referring to FIG. 5a, an exemplary flow diagram for determining and improving the usefulness of the curve fitting equation is shown therein. A routine begins at operation 402, where the sensor 140 is exposed to a sample containing the analyte. As described above, the electrochemical sensor 140 may be responsive to the levels of concentration of an analyte within the sample.

From operation 402, the routine proceeds to operation 404, where the sensor 140 may generate one or more data signals in response to the exposure to the analyte. In various embodiments, the data signals may be in the form of a voltage, current, charge, or any other type of measurable output. These data signals are continuously being generated by the sensor 140 while being exposed to the analyte. The routine then proceeds through operations 406 to 410, as described herein above.

From operation 410, the routine proceeds to operation 415 in which a curve fitting equation is determined for the selected data points. The curve fitting equation may be determined by conventional methods such as, but not limited to, regression analysis or the least square methods. According to various embodiments, the curve fitting equation may typically be a second degree logarithmic equation that has a general form of $$s(t)=a(\log(t))^2+b(\log(t))+c,$$

where a, b, and c are the polynomial coefficients that are determined based on the converted data points, and s(t) is the calculated sensor output at a particular time t. In one embodiment, a predetermined value of the logarithm of time at which a critical point occurs is provided, the predetermined value providing a relationship between polynomial coefficients. The precise values of a, b, and c, which are determined experimentally or analytically (for example, using regression analysis) for each sensor configuration used, depend in part upon the concentration of the analyte, the size of the sample, the temperature, the geometry of the sensor transducer setup, and other parameters. In one instance, the critical point is an local extremum point, and the predetermined value (V) provides a relationship between the fit parameters b and a of the form b=−2 aV, the fit parameters a and c being determined based on the sensor response.

From operation 415, the routine proceeds to operation 416, where the extrapolation module 120 extrapolates the calculated end point response of the sensor 140 by solving the curve fitting equation for a time that falls within the equilibrium region. From operation 416, the routine proceeds to operation 430 in which the curve fit quality module 126 determines and improves the usefulness of the curve fitting equation. Embodiments of the logic flow diagram for operation 430 are shown in FIGS. 6a, 6b, 7a, 7c.

Figure 5B:
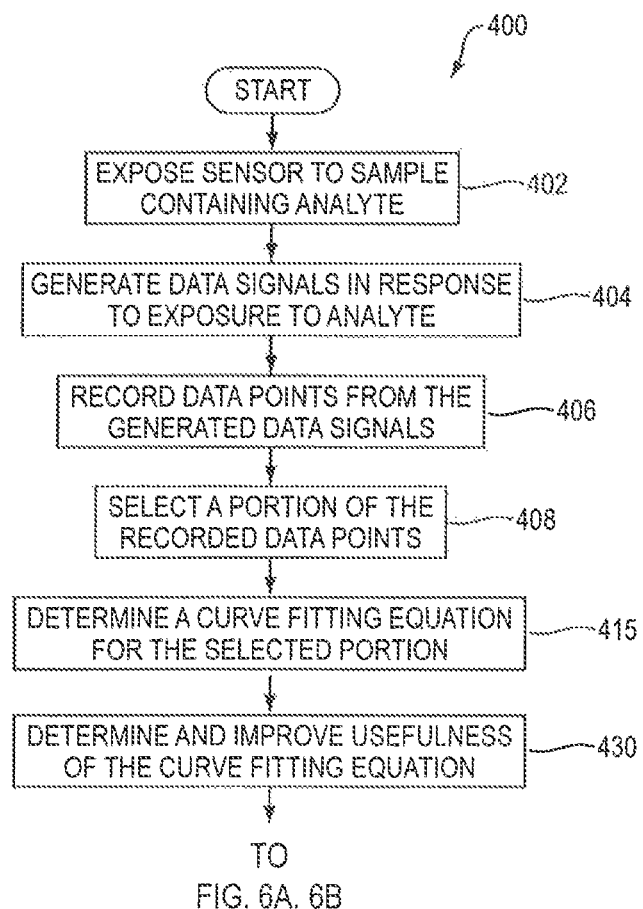

Another embodiment of the logic flow diagram for analyzing data for an analyte is presented in FIG. 5b. As stated above, embodiments in which only some of the modules in the analyte concentration measurement system shown in FIG. 1 are used are within the scope of this invention. There are numerous analyte concentration measurement systems in which a curve describing a fit for the data points can be used even if the curve fitting equation is not used for extrapolation. In the embodiment shown in FIG. 5b, operation 416 is omitted to emphasize that embodiments in which extrapolation is not present are also within the scope of these teachings.

Figure 6A:
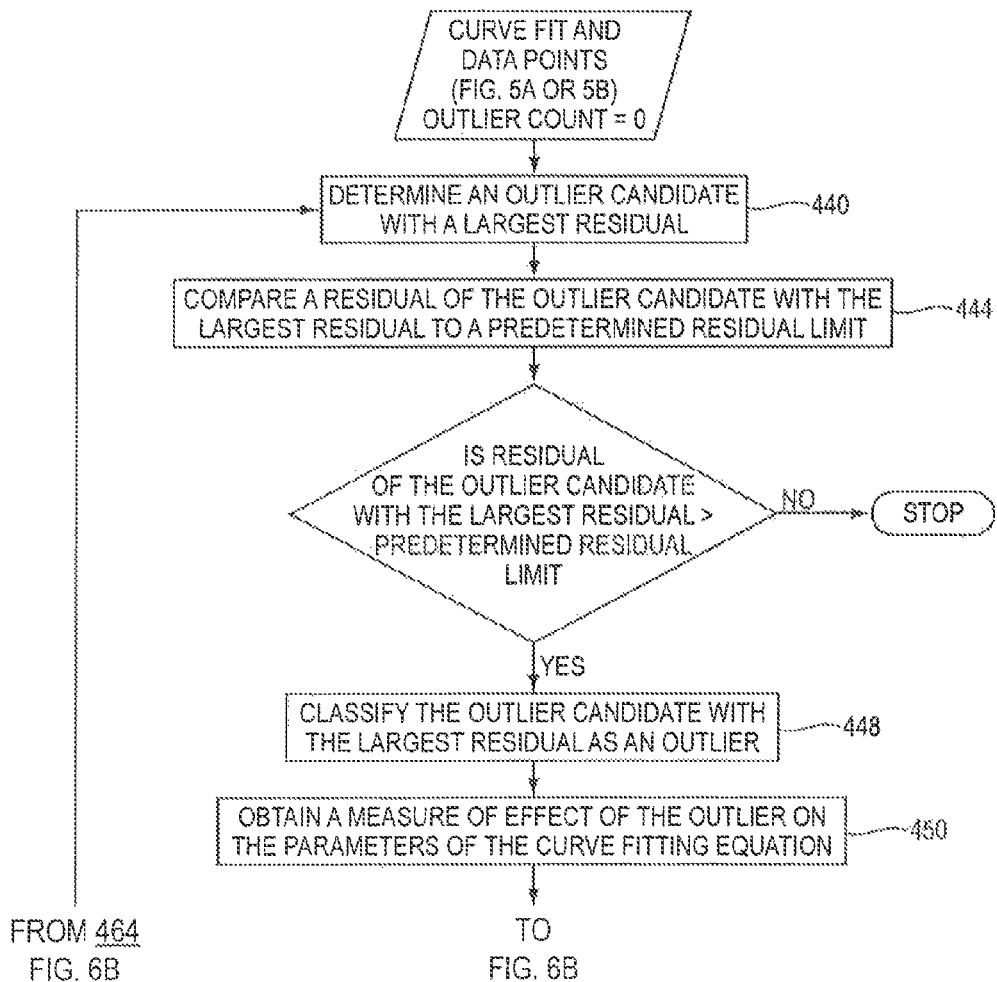
FIGS. 6a and 6b are exemplary logical flow diagram for determining and improving usefulness of the curve fitting equation according to embodiments of the invention.
Figure 6B:
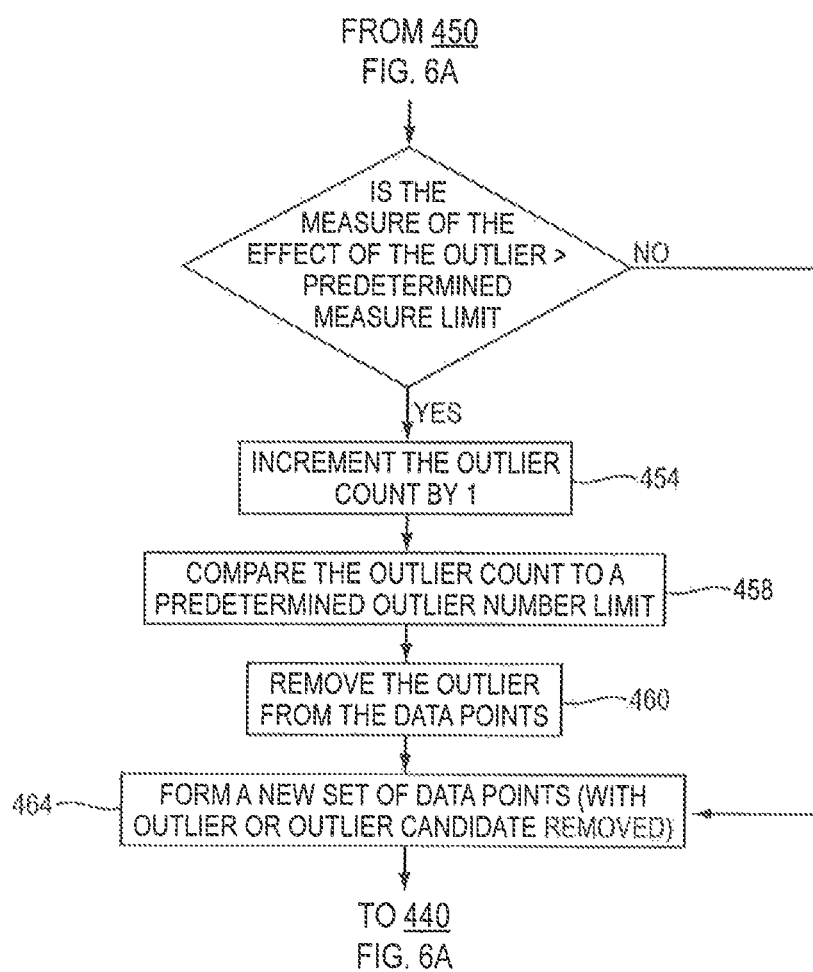

One embodiment of the logic flow diagram for determining and improving the usefulness of the curve fitting equation is shown in FIGS. 6a and 6b. Referring to FIG. 6a, the logic flow diagram shown therein starts from the curve fit and data points obtained from the flow diagram shown in FIG. 5a or 5b or equivalently obtained from the data point recording module 114, data point selection module 116 and curve fitting module 118 in FIG. 1. The outlier count is initially set to zero. An outlier candidate with the largest residual is determined (operation 440). The logic flow diagram then proceeds to comparing the residual of the outlier candidate with a predetermined residual limit (operation 444). The residual of the outlier candidate is then compared to a predetermined residual limit. If the residual of the outlier candidate with the largest residual is less than or equal to the predetermined residual limit, the operation stops since any other outlier candidate will have a smaller residual and would be within the predetermined residual limit. If the residual of the outlier candidate is greater than the predetermined residual limit, the outlier candidate with the largest residual is classified as an outlier (operation 448). The logic flow diagram then proceeds to obtain a measure of the effect of the outlier on the parameters of the curve fitting equation (operation 450). The logic flow diagram is continued in FIG. 6b. Referring to FIG. 6b, the measure of the effect of the outlier on the parameters of the curve fitting equation, obtained in operation 450, is compared to the predetermined measure limit. If the comparison of the measure of the effect of the outlier on the parameters of the curve fitting equation with the predetermined measure limit indicates that the outlier has a significant effect on the parameters of the curve fitting equation, the outlier count is incremented by one (operation 454), the outlier count is compared to a predetermined outlier numbers limit (operation 458) and the outlier is removed from the data points (operation 460). If the outlier count is greater than the outlier number, the data set is identified for review. The logic flow diagram then forms a new set of data points with the outlier removed (operation 464), in one instance, a new set of curve fit parameters for the curve fitting equation are obtained using the new set of data points in the curve fitting module 118. The logic flow diagram then returns to determining a new outlier candidate with largest residual for the new data set of data points (operation 440, FIG. 6a). If the comparison of the measure of the effect of the outlier on the parameters of the curve fitting equation with the predetermined measure limit indicates that the outlier does not have a significant effect on the parameters of the curve fitting equation, the logic flow diagram proceeds to forming a new data set of points with the outlier candidate removed (operation 464). In one instance, a new set of curve fit parameters for the curve fitting equation are obtained using the new set of data points in the curve fitting module 118. The logic flow diagram then returns to determining a new outlier candidate with largest residual for the new data set of data points (operation 440, FIG. 6a). The routine proceeds until all outliers have been identified although it could be stopped if the outlier count exceeds the predetermined outlier number limit.

Figure 7A:
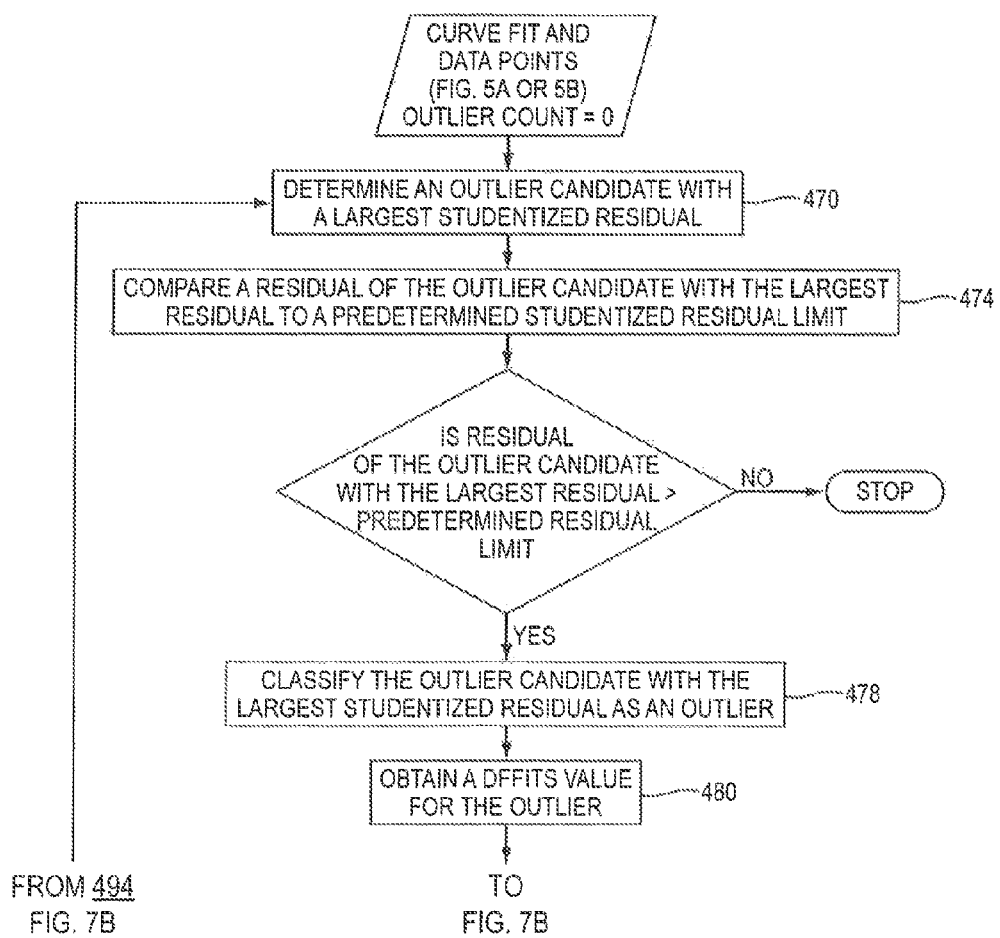
FIGS. 7a and 7b are other exemplary logical flow diagram for determining and improving usefulness of the curve fitting equation according to exemplary embodiments of the invention.
Figure 7B:
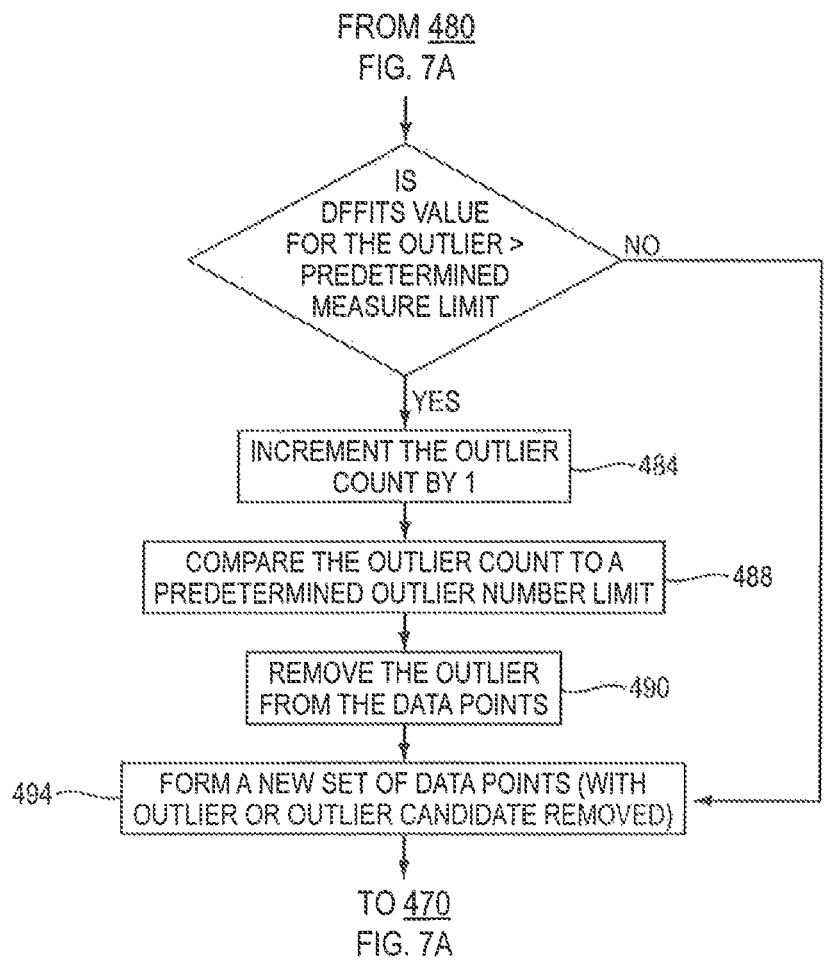

An exemplary embodiment of the logic flow diagram for determining and improving the usefulness of the curve fitting equation is shown in FIGS. 7a and 7b. Referring to FIG. 7a, the logic flow diagram shown therein starts from the curve fit and data points obtained from the flow diagram shown in FIG. 5a or 5b or equivalently obtained from the data point recording module 114, data point selection module 116 and curve fitting module 118 in FIG. 1. The outlier count is initially set to zero. The outlier count is initially set to zero. An outlier candidate with the largest Studentized residual is determined (operation 470). The logic flow diagram then proceeds to comparing the Studentized residual of the outlier candidate with a predetermined Studentized residual limit (operation 474). If the Studentized residual of the outlier candidate with the largest Studentized residual is less than or equal to the predetermined Studentized residual limit, the operation stops since any other outlier candidate will have a smaller Studentized residual and would be within the predetermined residual limit. If the Studentized residual of the outlier candidate is greater than the predetermined Studentized residual limit, the outlier candidate with the largest Studentized residual is classified as an outlier (operation 478). The logic flow diagram then proceeds to obtain a REFITS value for the outlier (operation 480). The logic flow diagram is continued in FIG. 6b. Referring to FIG. 7b, the DFFITS value for the outlier, obtained in operation 480, is compared to the predetermined DFFITS limit. If the comparison of the DFFITS value for the outlier with the predetermined DFFITS limit indicates that the outlier has a significant effect on the parameters of the curve fitting equation, the outlier count is incremented by one (operation 484), the outlier count is compared to a predetermined outlier numbers limit (operation 488) and the outlier is removed from the data points (operation 490). If the outlier count is greater than the outlier number, the data set is identified for review. The logic flow diagram then forms a new data set of points with the outlier removed (operation 494). In one instance, a new set of curve fit parameters for the curve fitting equation are obtained using the new set of data points in the curve fitting module 118. The logic flow diagram then returns to determining a new outlier candidate with largest Studentized residual for the new data set of data points (operation 470, FIG. 7a). If the comparison of the DFFITS value for the outlier with the predetermined DFFITS limit indicates that the outlier does not have a significant effect on the parameters of the curve fitting equation, the logic flow diagram proceeds to forming a new data set of points with the outlier candidate removed (operation 494). In one instance, a new set of curve fit parameters for the curve fitting equation are obtained using the new set of data points in the curve fitting module 118. The logic flow diagram then returns to determining a new outlier candidate with largest residual for the new data set of data points (operation 470, FIG. 7a). The routine proceeds until all outliers have been identified although the routine could be stopped if the outlier count exceeds the predetermined outlier number limit.

Figure 8A:
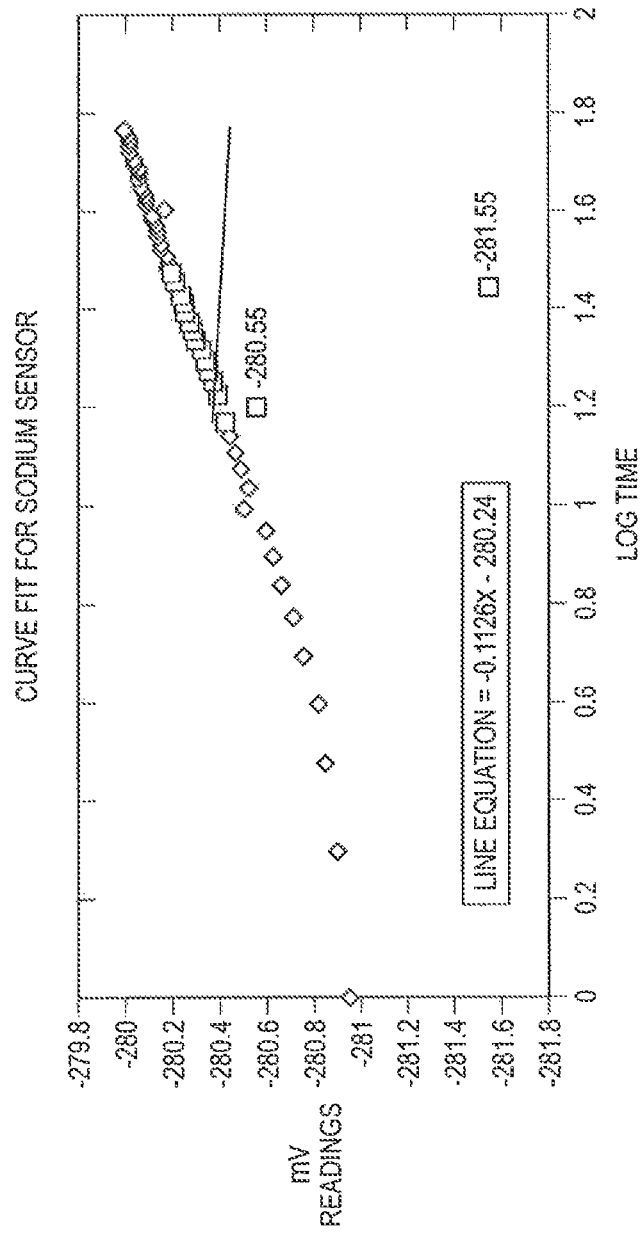
FIGS. 8a, 8b and 8c show an exemplary graphical representations of voltage versus time for experimental data generated by a sensor for measuring the concentration of sodium according to one embodiment of the invention.

An exemplary graphical representation of voltage versus time for experimental data generated by a sensor measuring sodium concentration is shown in FIG. 8a. The exemplary graphical representation shows a series of data points capture from a data signal generated by a sodium sensor 140. The data points shown therein indicate an output value which for the exemplary graphical representation is shown in m Volts. A curve fitting equation, of the type $ax^2+bx+c$ with $a=0$, is obtained from a curve fitting module 118. For the exemplary graphical representation shown there in the curve fitting equation is $-0.1126x-280.24$. In the exemplary embodiment disclosed herein below determining an outlier candidate with the largest residual is performed by determining a data point with a largest Studentized residual and obtaining a measure of the effect of the outlier is performed by obtaining a DFFITS value (DFFITS, in this exemplary embodiment, refers to the measure that indicates the change at an extrapolated point caused by removing an individual point from the regression fit.) The absolute value Studentized residual limit is 5; Studentized residuals having an absolute value higher than the one we consider outliers. The absolute value of the DFFITS limit is 0.04; any DFFITS absolute value higher than this limit will indicate that the outlier has a significant effect on the parameters of the curve fitting equation and should be removed. The maximum number of outliers is set equal to 2. Is the sample has more than two outliers, the sample will be set aside for review since it may be considered to be in error. Table 1 below displays the sensor output, Studentized residuals and DFFITS values for each update times in which the measurement was taken.

TABLE 1

| Time (s) | Log time | sensor output (mV) | Studentized Res. | DFFIT (delta55) |
|---|---|---|---|---|
| 15 | 1.176091 | −280.41814 | −0.167969237 | 0.02924 |
| 16 | 1.20412 | −280.55 | −0.584557754 | 0.07786 |
| 17 | 1.230449 | −280.38466 | −0.031943123 | 0.00324 |
| 18 | 1.255273 | −280.36149 | 0.048486072 | −0.00351 |
| 19 | 1.278754 | −280.34518 | 0.105178236 | −0.00484 |
| 20 | 1.30103 | −280.33188 | 0.151657918 | −0.00331 |
| 21 | 1.322219 | −280.30999 | 0.223545623 | 0.00016 |
| 22 | 1.342423 | −280.29411 | 0.277612041 | 0.00612 |
| 23 | 1.361728 | −280.27652 | 0.337580624 | 0.01431 |
| 24 | 1.380211 | −280.26493 | 0.380544209 | 0.02363 |
| 25 | 1.39794 | −280.24605 | 0.447273738 | 0.03632 |
| 26 | 1.414973 | −280.23704 | 0.485403754 | 0.04858 |
| 27 | 1.431364 | −280.22931 | 0.521192884 | 0.06190 |
| 28 | 1.447158 | −281.55 | −33.69556139 | −0.49856 |
| 29 | 1.462398 | −280.20571 | 0.625390089 | 0.09754 |
| 30 | 1.477121 | −280.18897 | 0.698680225 | 0.12198 |

As can be seen from Table 1, the Studentized residual at time 28 seconds has the maximum absolute value, −33.7, and the Studentized residual with the maximum absolute value is higher than the Studentized residual absolutely limit. The value at time 28 seconds is classified as an outlier. The DFFITS value for the Studentized residual with the maximum absolute value is 0.499 and is outside the DFFITS limit. The outlier is then removed. The outlier count is set to 1.

Figure 8B:
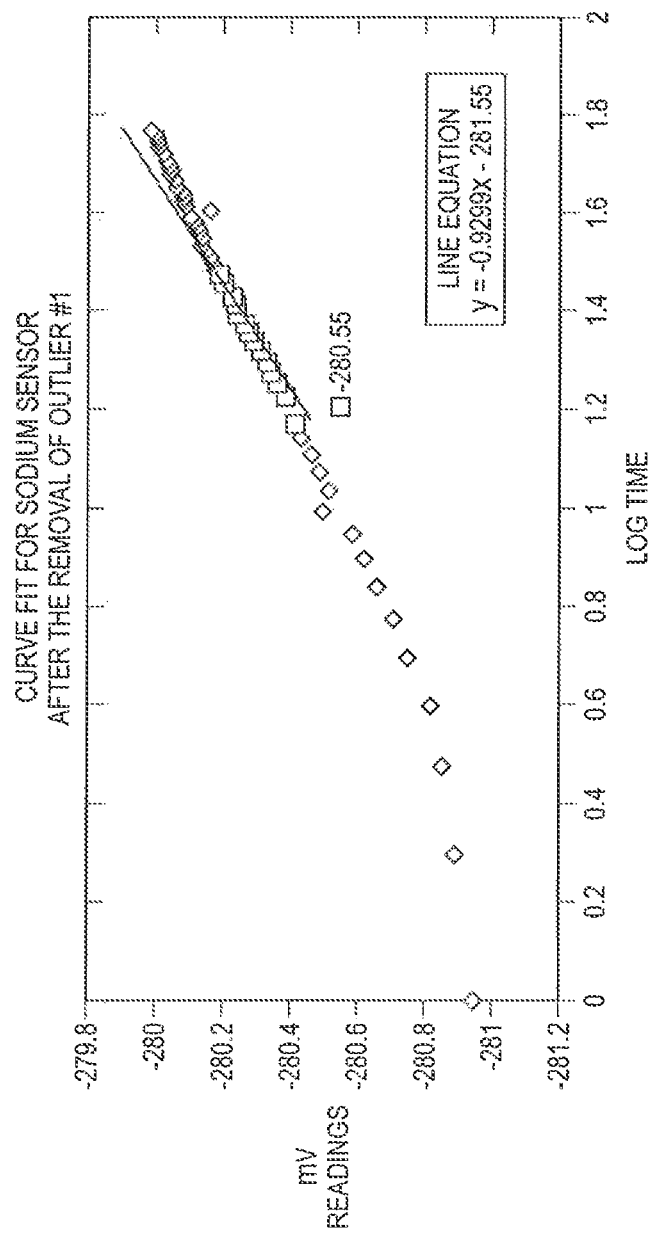

FIG. 8b shows the exemplary graphical representation of the data in FIG. 8a with the outlier at time 28 seconds removed. A curve fitting equation, of the type $ax^2+bx+c$ with a=0, is obtained from a curve fitting module 118 for the data set with the outlier at time 28 seconds removed. For the exemplary graphical representation shown there in the curve fitting equation is 0.9299x−281.55. As can be seen from Table 2 below, the Studentized residual at time 16 seconds has the maximum absolute value, −38.7, and the Studentized residual with the maximum absolute value is higher than the Studentized residual absolutely limit. The value at time 16 seconds is classified as an outlier. The DFFITS value for the Studentized residual with the maximum absolute value is −0.5 and is outside the DFFITS limit. The outlier is then removed. The outlier count is set to 2.

TABLE 2

| Time (s) | Log time | sensor output (mV) | Studentized Res. | DFFIT (delta55) |
|---|---|---|---|---|
| 15 | 1.176091 | −280.41814 | 1.302207232 | −0.02519 |
| 16 | 1.20412 | −280.55 | −38.75323932 | 0.05453 |
| 17 | 1.230449 | −280.38466 | 0.659093643 | −0.00758 |
| 18 | 1.255273 | −280.36149 | 0.646980468 | −0.00515 |
| 19 | 1.278754 | −280.34518 | 0.480296708 | −0.00232 |
| 20 | 1.30103 | −280.33188 | 0.271488649 | −0.00051 |
| 21 | 1.322219 | −280.30999 | 0.329904217 | 0.00029 |
| 22 | 1.342423 | −280.29411 | 0.250562512 | 0.00088 |
| 23 | 1.361728 | −280.27652 | 0.241429866 | 0.00146 |
| 24 | 1.380211 | −280.26493 | 0.090161186 | 0.00077 |
| 25 | 1.39794 | −280.24605 | 0.156690447 | 0.00172 |
| 26 | 1.414973 | −280.23704 | −0.030955726 | −0.00041 |
| 27 | 1.431364 | −280.22931 | −0.242884222 | −0.00383 |
| 28 | 1.447158 | | | |
| 29 | 1.462398 | −280.20571 | −0.406073413 | −0.00749 |
| 30 | 1.477121 | −280.18897 | −0.322605674 | −0.00679 |

Figure 8C:
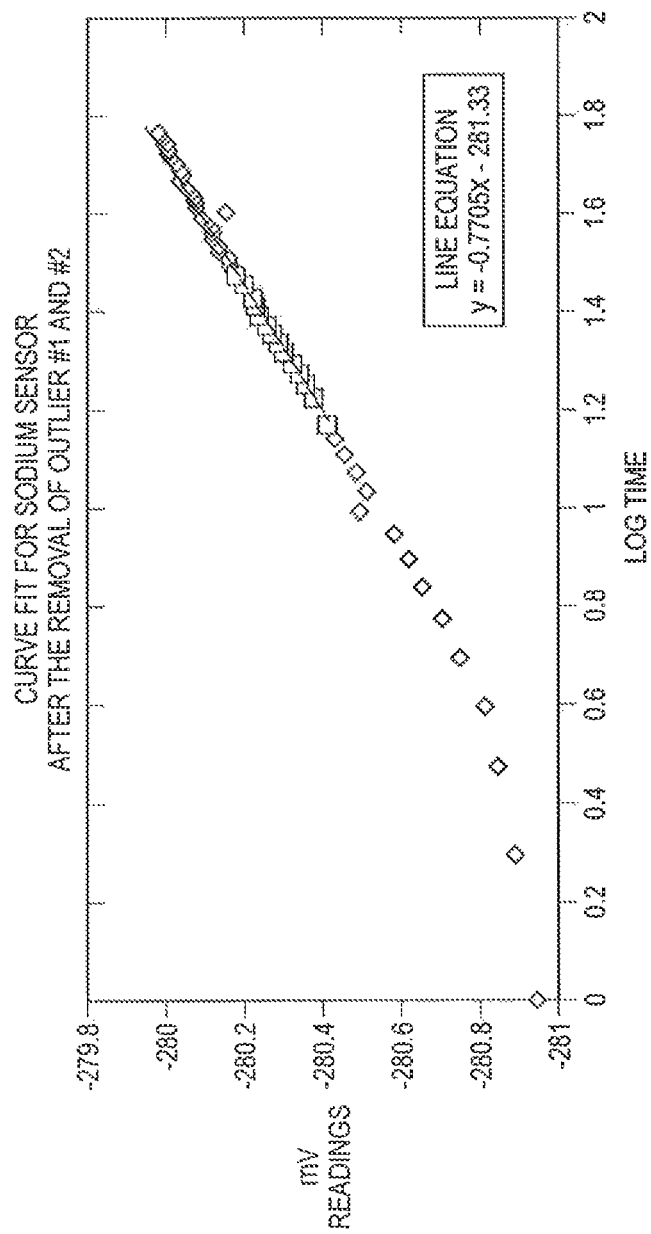

FIG. 8c shows the exemplary graphical representation of the data in FIG. 8a with the outlier at time 28 seconds removed and the outlier at time 16 seconds removed. A curve fitting equation, of the type $ax^2+bx+c$ with a=0, is obtained from a curve fitting module 118 for the data set with the outlier at time 28 seconds removed and the outlier at time 16 seconds removed. For the exemplary graphical representation shown there in the curve fitting equation is 0.7705x−281.33. As can be seen from Table 3 below, all the Studentized Residual values are within the limit and no DFFITS calculation are required. The outlier count is not higher than the outlier number limit.

TABLE 3

| Time (s) | Log time | sensor output (mV) | Studentized Res. | DFFIT (delta55) |
|---|---|---|---|---|
| 15 | 1.176091 | −280.41814 | −0.355455044 | not required |
| 16 | 1.20412 | | | not required |
| 17 | 1.230449 | −280.38466 | 0.170223356 | not required |
| 18 | 1.255273 | −280.36149 | −0.082739835 | not required |
| 19 | 1.278754 | −280.34518 | 0.02875639 | not required |
| 20 | 1.30103 | −280.33188 | 0.27049187 | not required |
| 21 | 1.322219 | −280.30999 | −0.077578419 | not required |
| 22 | 1.342423 | −280.29411 | −0.097178392 | not required |
| 23 | 1.361728 | −280.27652 | −0.267056658 | not required |
| 24 | 1.380211 | −280.26493 | −0.101176941 | not required |

TABLE 3-continued

| Time (s) | Log time | sensor output (mV) | Studentized Res. | DFFIT (delta55) |
|---|---|---|---|---|
| 25 | 1.39794 | −280.24605 | −0.427747325 | not required |
| 26 | 1.414973 | −280.23704 | −0.170357329 | not required |
| 27 | 1.431364 | −280.22931 | 0.136120199 | not required |
| 28 | 1.447158 | | | not required |
| 29 | 1.462398 | −280.20571 | 0.155631715 | not required |
| 30 | 1.477121 | −280.18897 | −0.181933585 | not required |

After the outlier detection is completed, each fit parameter from the last group of fit parameters, a=0, b=0.7705 and c=−281.33, is compared to the corresponding fit parameter limits, if any one of the parameters is outside the fit parameter limits for that parameter, the sample will be set aside for review since it may be considered to be in error. If all of the three parameters are within the corresponding fit parameter limit, extrapolation will take place and the results for the sample will be reported. For the exemplary embodiment shown in FIGS. 8a-8c, the fit parameter limits for parameter "b" are from 0.6 to 1.0 and the fit parameter limits for parameter "c" are from −290 to −260. Comparing each of the fit parameters from the last group of fit parameters, a=0, b=0.7705 and c=−281.33, to the fit parameter limits, each one of the each of the fit parameters from the last group of fit parameters is within the corresponding fit parameter limit. The sample value would be then reported. It should be noted that if the fit parameters from the first two groups of fit parameters had been compared to the corresponding fit parameter limits, they fit parameters would have been found to be outside of the fit parameter limits According to various embodiments, the disclosure presented herein may be utilized to reduce the time for determining an important response time of electrochemical sensors. In some embodiments, the electrochemical sensors may be used in a diffusion control response environment such as to calculate concentration levels of pO2, pCO2, glucose and lactate. In addition, the methodology may also be used for the end point detection of ion selective electrodes, such as and Na, K, Cl and Ca. Although some sensors typically exhibit fast responses and therefore an endpoint sensor response prediction may not be necessary, a curve fit may still be useful and the determination and improvement of the curve fit equation is still of importance.

What is claimed is:

1. A system for increasing sample throughput, comprising:
a sensor configured to generate data signals in response to being exposed to an analyte within a sample; and
a processor configured to record data points associated with the data signals, select a series of data points corresponding to a portion of a kinetic region time range from the recorded data points, determine a curve fitting equation that fits the series of data as a logarithmic scale of time wherein the curve fitting equation is of the form s(t)=a*(log(t))^2−2 aV(log(t))+c, and V is a log of a time which extremum occurs, wherein t represents time and a and c are fit parameters for a second order polynomial, extrapolate an end point response of the sensor using the curve fitting equation, and calculate, using the extrapolated end point response, a value corresponding to the analyte, thereby increasing said sample throughput, wherein the processor is configured to determine and improve usefulness of the curve fitting equation corresponding to the analyte by removing numerically distant data points, thereby constituting an analyzed set of data points, and determining another curve fitting equation that fits the analyzed series of data points as a logarithmic scale of time.

2. The system of claim 1, wherein the data points are recorded at equal intervals.

3. The system of claim 1, wherein the kinetic region time range extends from a first time when the sensor is first exposed to the analyte to a second time when the data signals generated by the sensor are substantially similar to an actual end point response of the sensor.

4. The system of claim 1, wherein extrapolating an end point response of the sensor using the curve fitting equation comprises solving the curve fitting equation for a time when then the data signals generated by the sensor are substantially similar to an actual end point response of the sensor.

5. The system of claim 1, wherein the processor is further configured to:
   determine a concentration of the analyte using the calculated end point response; and
   present the determined concentration of the analyte.

6. A system for analyzing samples, comprising:
   a sensor configured to generate data signals in response to being exposed to an analyte within a sample; and
   a processor configured to:
   record data points associated with the data signals, select a series of data points corresponding to a portion of a kinetic region time range from the recorded data points, determine a curve fitting equation that fits the series of data points as a logarithmic scale of time, wherein the curve fitting equation is of the form $s(t)=a*(\log(t))^2-2aV(\log(t))+c$, and V is a log of a time which extremum occurs, wherein t represents time and a and c are fit parameters for a second order polynomial; and
   determine and improve usefulness of the curve fitting equation corresponding to the analyte by removing numerically distant data points, thereby constituting an analyzed set of data points, and determining another curve fitting equation that fits the analyzed series of data points as a logarithmic scale of time, thereby increasing sample throughput.

7. The system of claim 6, wherein determining and improving usefulness of the curve fitting equation comprises:
   a) determining an outlier candidate with a largest residual;
   b) comparing a residual of the outlier candidate with the largest residual to a predetermined residual limit;
   c) classifying the outlier candidate with the largest residual as an outlier if the residual of the outlier candidate with the largest residual is greater than the predetermined residual limit;
   d) obtaining a measure of effect of the outlier on the parameters of the curve fitting equation;
   e) comparing the measure of the effect of the outlier to a predetermined measure limit;
   f) incrementing an outlier count, if the measure of the effect of the outlier is greater than the predetermined measure limit;
   g) comparing the outlier count to a predetermined outlier number limit, if the measure of the effect of the outlier is greater than the predetermined measure limit; and
   h) removing the outlier from the data points, if the measure of the effect of the outlier is greater than the predetermined measure limit, resulting in the analyzed set of data points;
   i) determine, if the measure of the effect of the outlier is greater than the predetermined measure limit, a curve fitting equation that fits the analyzed set of data points as a logarithmic function of time;
   j) repeat, if the measure of the effect of the outlier is greater than the predetermined measure limit, steps a) to h) for the analyzed set of data points; and
   k) identify the data points for review, if the outlier count is greater than the predetermined outlier number limit.

8. The system of claim 6, wherein the processor is further configured to:
   form an iteration set of data points by removing the outlier from the data points, if the measure of the effect of the outlier is at most equal to the predetermined measure limit;
   determine a curve fitting equation that fits a series of data from the analyzed set of data points as a function of time; and
   determine a curve fitting equation that fits a series of data from the iteration set of data points as a function of time; and
   i) repeat steps a) to h) for the iteration set of data points.

9. The system of claim 6, wherein the processor is further configured to:
   comparing each one fit parameter from a set of fit parameters for the curve fitting equation to a predetermined fit parameter limit for said one fit parameter; and
   identify the data points for review, if at least one fit parameter from the set of fit parameters is greater than the predetermined fit parameter limit for said one fit parameter.

10. The system of claim 7 wherein determining the outlier candidate with the largest residual comprises determining a data point with a largest Studentized residual; and wherein obtaining a measure of the effect of the outlier comprises obtaining a DFFITS value.

* * * * *

UNITED STATES PATENT AND TRADEMARK OFFICE
CERTIFICATE OF CORRECTION

PATENT NO. : 9,910,966 B2
APPLICATION NO. : 14/800846
DATED : March 6, 2018
INVENTOR(S) : Sohrab Mansouri, Jose Maria Cervera and Ashley Moraski It is certified that error appears in the above-identified patent and that said Letters Patent is hereby corrected as shown below:

On the Title Page

Delete:
(73) "Instruments",
And insert:
(73) --Instrumentation--.

Signed and Sealed this
Twenty-fourth Day of July, 2018

Andrei Iancu
*Director of the United States Patent and Trademark Office*